US00PP12426P2

(12) United States Plant Patent
Kumar et al.

(10) Patent No.: US PP12,426 P2
(45) Date of Patent: Feb. 26, 2002

(54) MINT PLANT NAMED 'KOSI'

(75) Inventors: Sushil Kumar; Nirmal Kumar Patra; Hemendra Pratap Singh; Alok Kalra; Harikesh Bahadur Singh; Paltoo Ram; Ved Ram Singh; Nareshwar Mengi; Vijay Pal Singh; Muni Ram; Ram Sajivan Shukla; Kambod Singh; Aparbal Singh; Suman Preet Singh Khanuja; Ajit Kumar Shasany; Arif Ali Naqvi; Birendra Kumar; Man Singh; Dharmendra Kumar Rajput; Raja Ram; Jitendra Pal Singh; Vijay Kumar; Hasan Tanveer; Sheo Ram Sharma, all of Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/145,546

(22) Filed: Sep. 2, 1998

(30) Foreign Application Priority Data

Jun. 3, 1998 (IN) ..... 1510/DEL/98

(51) Int. Cl.[7] ..... A01H 5/00
(52) U.S. Cl. ..... Plt./259
(58) Field of Search ..... Plt./259

(56) References Cited

U.S. PATENT DOCUMENTS

PP10,935 P * 6/1999 Kumar et al. ..... Plt./259

OTHER PUBLICATIONS

Sushil Kumar et al.; Himalaya—a high menthol yielding hybrid clone of *Mentha arvensis*; Journal of Medicinal and Aromatic Plant Sciences 19 (1997) 729–731.

* cited by examiner

*Primary Examiner*—Bruce R. Campell
*Assistant Examiner*—W C Baker
(74) *Attorney, Agent, or Firm*—Dorsey & Whitney LLP

(57) ABSTRACT

A novel mint plant 'Kosi' characterized by its high menthol content, high biomass and high oil yield with symmetrical branching giving globular shape to the canopy for equal distribution of sunlight to the lower leaves.

3 Drawing Sheets

FIELD OF INVENTION

The present invention relates to a new and distinct variety of mint plant 'Kosi' of the species botanically known as *Mentha arvensis*. The new variety which has been named as 'Kosi' can be propagated vegetatively through suckers for commercial cultivation.

BACKGROUND OF THE INVENTION

Mint plant *Mentha arvensis* is cultivated commercially in tropical and subtropical climates. The oil and the oil products of this plant have the highest share in mint trade. The oil is used mainly for producing menthol and the by-product dementholised oil (DMO) also finds uses in pharamceutical and cosmetic industry. Menthol has a cooling, refreshing aroma and antiseptic properties. The derivatives of menthol are also used in flavoring confectionary and cigarette. The commercial potential of "menthol" in the market gives an incentive for breeders to develop high-menthol yielding mint plants.

Recently, Central Institute of Medicinal and Aromatic Plants (CIMAP) has developed a high menthol containing Japanese mint plant (cv 'Himalaya'), which is hybrid between CIMAP/MAS9 and CIMAP/HY 77. The said mint plant *Mentha arvensis* 'Himilaya' is tolerant to common diseases afflicting mint plants and yields more oil than existing mint plants.

SUMMARY OF THE INVENTION

The present invention relates to a novel mint plant 'Kosi', characterized by its high biomass and high oil yield with synchronous branching giving globular shape to the canopy for equal distribution of sunlight to the lower leaves.

During their plant breeding and plant development programs, the Applicants found that arrangement of the leaves could affect the oil yield of the plants. Accordingly, it is an object of the present invention to develop a genotype with a special arrangement of the leaves so as to enable maximum harvest of the sunlight by the leaves due to minimum shading of lower leaves; thereby increasing foliage, thickness of the leaves, facilitating growth and preventing leaf fall.

Another object of the invention is to develop a high menthol containing mint plant with early maturing habit to fit different cropping systems. Yet another object of the invention was to retain the improved disease resistance, higher biomass, high oil content and high oil yield in the new genotype.

BRIEF DESCRIPTION OF THE DRAWINGS

In the drawings, which are a photographic illustration of the new variety.

DETAILED DESCRIPTION OF THE INVENTION

Figure 1:
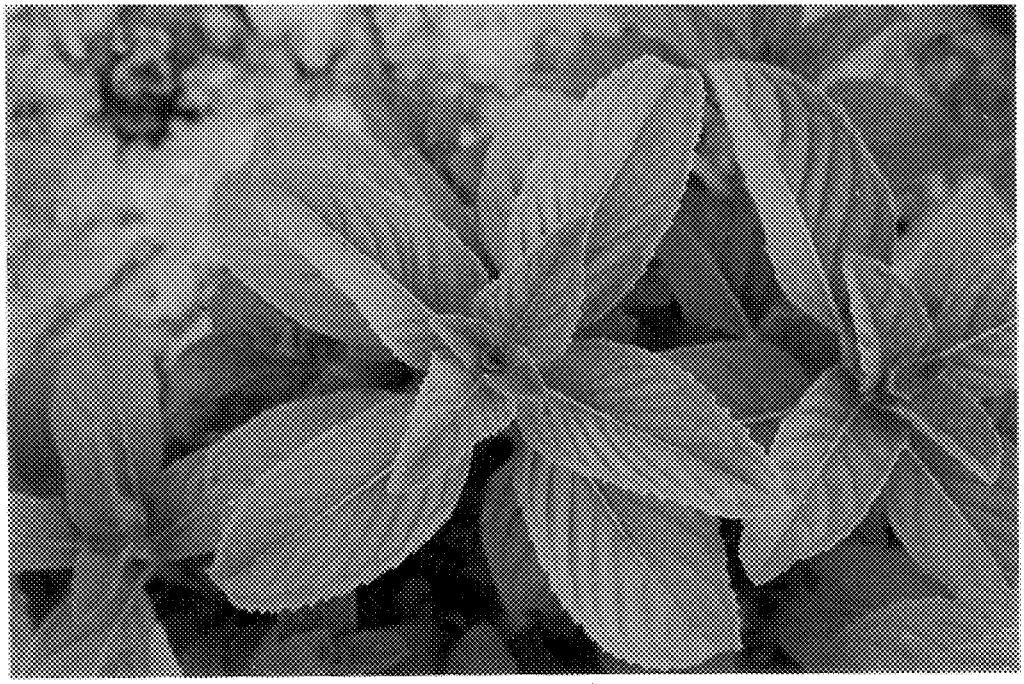
FIG. 1: shows the new genotype Kosi.

In accordance with the said objects and as a result of planned experiments involving open pollination, clonal propagation, comparative evaluation and selections the Applicants have developed a yet another new variety of mint plant which has greater foliage, is disease resistant and yields more oil than existing species of mint plants. The seedling population has been raised from open pollinated seeds of genotype CIMAP/HY-77 (cv 'Kalka' (U.S. patent application Ser No. 09/145,290)) which has a single (genotype) and such plant with an unusual phenotype of globular plant canopy, is not reported till now. The canopy and the arrangement of leaves being unique also constitutes an important feature facilitating maximal capture of sunlight, there is an increase in the total leaf biomass due to minimal shading of lower leaves. Further analysis in continuous evolution revealed several desirble features including higher biomass, better oil yield and quality, early maturing habit and resistance to leaf spot, rust and powdery mildew disease.

The genotype 'Kosi' developed by the Applicants is novel with respect of plant canopy which is an unique feature of harvesting the sunlight by the plant and thus increasing the biomass. The genotype is novel with respect to the RAPD pattern which is completely different in the present invention. As such, the new improved genotype is unique and distinct from other existing genotypes so far reported.

The new variety named as "Kosi" was developed at Central Institute of Medicinal and Aromatic Plants, Field Station Pantnagar U.S. Nagar, Uttar Pradesh, India. Kosi has been reproduced asexually by the under ground suckers over the years 1995–98 and the vegetative progeny derived through somatic (mitotic) cell division are indistinguishable from the original plant, developed and established through strategic half-sib progeny selection in the earlier variety (CIMAP/HY 77 (or Kalka). As to the character of the area where the plant (Kosi) has been developed and asexually reproduced, it is situated at the subtropical foothill belt for the mail mint growing area of northern India. The soil of the experiment site at Pantnagar was clay-loam in texture, high in organic carbon (1.14%), medium in available P(180.0 Kg/ha) and K (200.0 Kg/ha) with pH7.1. The area being located at a latitude of 29° N, longitude of 79.30E and at the altitude of 244 above the mean sea level, it enjoys the minimum temperature ranging between 3–8° C. and the maximum temperature ranging between 17–25° C. during winter months, when the mint crops grow their underground suckers (the plant propagules). The corresponding ranges for minimum and maximum temperature, which the crop usually receives during its growth period in spring and summer, are 9–25° C. and 25–42° C., respectively. The total rainfall over the area in different months of the years during 1994–98 ranged between 1.2 mm. (During winter) to 333.0 mm. (During rains), the rainfall during the crop growing period (Feb-June) being recorded as 2.4 mm to 91.8 mm.

Accordingly, the invention provides a new and distinct variety 'Kosi' having the following combination of characters as distinct from the known varieties of *Mentha arvensis:*

1. Light greenish leaves, whitish flowers and branching providing a globular canopy allowing equal distribution of sunlight, thus prevents yellowing and fall of lower leaves.
2. Early maturing period (90 to 100 days).
3. Better tolerance to leaf spot, rust and powdery mildew.
4. Randomly amplified polymorphic DNA (RAPD) profile, for polymerized chain reaction (PCR) amplified DNA segment using 12 primers, distinct from any other known to us.
5. Higher herbage, oil yield and menthol content as compared to any other existing varieties. Kosi can be taxonomically described in the following manner:

1. Genus: Mentha.
2. Species: *arvensis* L.
3. Family: Lamiaceae.
4. Common name: Japanese mint/corn mint/menthol mint.
5. Growth habit: Erect, with very regular and symmetric growth habit in the aerial stems, branches and leaves giving a globular shape to the plant canopy.
6. Stem: Quadrangular, pubescent, hard, woody, yellowish green (144C), faint purplish red (69A) pigments at the base 5–7 mm thick at the fifth internode.
7. Number of internodes: 30 to 35.
8. Length of internodes: 3.50 to 4.0 cm.
9. Leaf:
   *Colour.*—Light green (137 C).
   *Arrangement.*—Opposite, exstipulate and simple.
   *Texture.*—Moderately thick and rigid.
   *Surface.*—Moderately hairy with glandular trichomes (the sides for essential oil synthesis) in both sides; ventral surface with more trichomes.
   *Shape.*—Lanceolate.
   *Tip.*—Acute.
   *Base.*—Attenuate.
   *Size.*—Moderately broad.
   *Petiole length.*—1.0–1.5 cm.
   *Area.*—12.2 $cm^2$.
   *Length.*—8.0 cm.
   *Width.*—3.0 cm.
   *Margin.*—Shallow serration with 30 to 56 teeth.
10. Leaf: Stem ratio: 1.5.
11. Inflorescence: Verticillate (cymes).

Each cyme comprises 20 to 30 florets as against 15–20 in the varieties Himalaya and Shivalik; cymes occur in the leaf axils and form a whorl of florets around the stem.

12. Flowers (florets): Very small in size, perfect, hermaphrodite, nearly actinomorphic and hypogynous.

*Pedicel.*—1.5 to 2.0 mm in length, Yellow green (145C).
   *Calyx.*—Four sepals, persistent, 2 to 3 mm in length, Narrowly deltoid and acuminate, Yellow green (145B).
   *Corrolla.*—Whitish purple (76D) 4.0 to 5.0 mm in length, composed of 4 petals, differentiated into tube and a limb (tube due to fusion of the petals at their base.).
   *Anthers.*—Four, ocidimetary, white, remain inside the corolla tube.
   *Stigma.*—Bifid, bicarpellary syncarpous; Ovary superior, deeply four-lobed, bilocular; Placentation axile; Style gynobasic arising between the lobes of the ovary.
   *Fruit and seeds.*—The fruit is of four one-seeded nutlets enclosed by the persistent calyx, The seeds with a scanty endosperm and straight embryo; The seeds brown, minute in size.

The genotype Kosi is a herbaceous perennial with upright stems coming out of underground rhizomes (suckers) growing laterally. The stems grow erect with symmetrical mode of branching in regular fashion at the leaf axils giving a globular look which is helpful for sun light harvesting. The new genotype Kosi in contrast to the other standard varieties like CIMAP/Shivalik, CIMAP/Kalka and CIMAP/Himalaya profusely flowering in the hot summer months (May and June), profusely flower late in the winter months (December–January) after its cutting (usually the aerial tops) are drawn from the field plantation during rains (after collection of the first harvest) and planted in field nursery during July–August to raise suckers (propagules) for the next mint crop. The span of flowering in Kosi is relatively short (15 days as against 25–30 days of the others). The flowering occurs in basipetal succession. The whitish purple florets are arranged in whorls in the inflorescence which arises from the nodes at the axil of leaves. The chromosome number is 2n=8x=96. The colour codes are in accordance with the "R.H.S. Colour Chart" published by The Royal Horticulture Society, 80 Vincent Square, London SWIP 2PE, 1995. Additional description in comparison to other genotypes is presented in the following examples.

During 1993–94 growing season a variant (VI) was identified in the field, planted with 18000 plants of the high yielding genotype CIMAP/HY 77 (or Kalka). The variant was having unique robust growth habit and higher biomass (2.50 Kg against 1.30 Kg of the normal plants as recorded after its harvesting. During the flowering of the population of CIMAP/HY 77, the variant was covered of about half of its flowering canopy by butter paper bags to collect selfed seeds leaving the rest half of the flowers unbagged to collect the open pollinated seeds. The bagged flowers of the variant did not show any seed setting indicating thereby that the variant does not set seeds under selfing. In the contrary the unbagged flowers of the variant exhibited a suitable quantity of seeds clearly indicting that the variant is endowed with the property of setting sexual seeds only under out crossings with other plants in the population. It may be pointed out that seed settings from natural outcrossings is not unusual for the Indian or mint, as it has recently been ascertained by the successful efforts in raising the high yielding variety Himalaya, the cross hybridization product of the two varieties. Gomti and Kalka (CIMAP HY 77) (Kumar et al., 1999; U.S. Plant Pat. No. 10,935). In view of complete absence of seed settings under selfing of the variant, the latter's open pollinated seeds could virtually be considered as the products (half-sibs) of the known female parent (i.e. the variant) and unknown male parent in the population of Kalka. The open pollinated seeds (half-sibs) of the variant were grown in a mininursery of glass house, out of which 25 $V_1$-half-sib plants were recovered. Subsequently all the 25 $V_1$-half-sib plants could be vegetatively multiplied by their underground suckers and that way a total of 25 $V_1$-half-sib progeny populations of the variant could be raised and established. To facilitate the morpho-physiological assessment of these half-sib progenies against their progenitor (the variant), the latter was vegetatively multiplied by the suckers. The derived clonal population ($V_1C$) comprised 80 plants. The clonal population ($V_1C$) of the variant did not differ much from the control CIMAP HY-77 for morpho-physiologiccal traits including oil content potential, whereas clonal populations drawn from the half-sibs of the variant showed in general, significant variations among them selfes, with their progenitor ($V_1$) and the control CIMAP/HY-77 (or Kalka) for oil content as well as other morpho-physiological attributes. Among the twenty five half-sibs, one (Kosi) appeared as very unusual genotype for the plant attrigutes, especially total biomass, oil content and oil yield. In contrast to the belief that total biomass and/or content in aromatic plants have negative associations with oil yield, Kosi registered high performances for all these three economic traits. In the subsequent two years (1994–95) and 1995–96) Kosi could be vegetatively multiplied and assessed for its performances during 1996 and 1997. After the selection trial the genotype was named as Kosi. The genotype showed better yield of herbage and oil when harvested after 90 to 110 days after planting in comparison to the other genotype tested.

The stems of the genotype 'Kosi' are 5–7 mm thick (at $5^{th}$ internode) and grow erect with symmetrical branching with a special arrangement of branches giving a globular look which is helpful for sunlight harvesting. There are two leaves at each node and 4 at the apex. The leaves are lanceolate in shape and arranged in opposite decussate phyllotaxy. The flowers are arranged in whorls in the inforescence which arises from the nodes at the axil of leaves. The chromosome number is 2n=96.

EXAMPLE 1

The growth performances of Kosi was compared against CIMAP/HY 77 (or Kalka), CIMAP/Shivalik and CIMAP/Himalaya. The result is presented in Table-1 which shows superior performance of the invented genotype. The genotype Kosi matures early in comparison to others, which is an advantage to fit this genotype in different cropping patterns in the country along with the food crops.

TABLE 1

| | (Amended): Average ± Critical Difference (CD) | | | |
|---|---|---|---|---|
| Trait | HY-77 (or Kalka) | Shivalik | Himalaya | Kosi |
| Plant height (cm) | 102 ± 1.9 | 93.0 ± 2.2 | 121.8 ± 2.6 | 119.2 ± 1.5 |
| Leaf length (cm) | 11.0 ± 0.6 | 8.8 ± 0.5 | 10.1 ± 0.3 | 8.0 ± 0.3 |
| Leaf width (cm) | 3.0 ± 0.4 | 5.0 ± 0.4 | 4.0 ± 0.5 | 3.0 ± 0.4 |
| Weight of single plant (g) | 225.3 ± 3.2 | 250.0 ± 7.0 | 307.4 ± 5.0 | 304.7 ± 4.8 |
| Leaf:Stem radio | 1.0 ± 0.1 | 0.8 ± 0.1 | 0.9 ± 0.2 | 1.40 ± 0.1 |
| Growth habit | Symmetrical | Asymmetrical | Somewhat | Bushy |

TABLE 1-continued

| Trait | (Amended): Average ± Critical Difference (CD) HY-77 (or Kalka) | Shivalik | Himalaya | Kosi |
|---|---|---|---|---|
| | and bushy | nonbushy | nonbushy | symmetrical |
| Shape of canopy | Somewhat dome shaped | Pyramidal shaped | Somewhat pyramidal | Completely dome shaped |
| Time of flowering | During hot summer (May–June) | During hot summer (May–June) | During hot summer (May–June) | During winter (December) |
| Span of flowering | 25 days | 30 days | 25 days | 15 days |
| Physiological maturity habit (for maximum growth in biomass, per se oil content, oil yield and oil quality but not for flowing and seed formation) | Normal (110 days) | Normal (110 days) | Normal (110 days) | Early (90–100 days) |

EXAMPLE 2

Initial trial during 1996 (planting date 22$^{nd}$ January) was conducted with fertilizer dose of 180:40:40 ($N_2$:$P_2$:$O_5$:$K_2O$) and the yield attributes were compared with CIMAP/HY-77(or Kalka). The results are presented in Table-2. The values in parenthesis indicate percent improvement over control CIMAP/HY-77. The plants were harvested 110 days after planting.

EXAMPLE 3

During 1997 (planting date 20$^{th}$ January) the yield trial of 'Kosi' was conducted as in Example 2 and yields were compared with CIMAP/Shivalik, CIMAP/HY-77, CIMAP/Himalaya, and CIMAP/Gomti. The results of yield trial are given in Table 3.

TABLE 2

| Genotype/ Variety | Herbage yield/plot (kg) | Herbage yield/ ha (Q) | Glass distilled oil content % | Glass distilled oil yield/ha (kg) | Single tank, field distilled oil yield plot (kg) | Field distilled oil yield/ha (kg) |
|---|---|---|---|---|---|---|
| HY-77 (control) | 550 | 163.70 | 0.75 | 122.76 | 3.6 | 107.15 |
| Kosi | 634 | 188.70 (15.3) | 1. (33.3) | 188.70 (53.7) | 5. | 148.82 (38.9) |

TABLE 3

| Name of the variety | Herb yield/plot (16 m × 5 m) (kg) | Herb yield/ha (Q) | Oil content (%) | Oil yield/ plot (kg) | Oil yield/ha (kg) | Per cent improvement in Kosi over the other varieties for Herb yield | Oil yield |
|---|---|---|---|---|---|---|---|
| Shivalik | 152.0 | 190.0 | 0.50 | 0.76 | 95.0 | 35.5 | 103.2 |
| HY-77 | 166.0 | 207.5 | 0.60 | 1.00 | 124.5 | 24.1 | 55.1 |
| Himalaya | 208.0 | 260.0 | 0.60 | 1.25 | 156.0 | −1.0 | 23.8 |
| Gomti | 202.0 | 252.5 | 0.36 | 0.73 | 91.0 | 2.0 | 112.2 |
| Kosi | 206.0 | 257.5 | 0.75 | 1.54 | 193.1 | — | — |
| CD (5%) | 10.64 | 12.58 | 0.04 | 0.232 | 12.73 | — | — |

EXAMPLE 4

Single tank based field distillation of the plant materials were carried out during 1997 (planting date 20$^{th}$ January), harvesting after 100 days for different CIMAP varieties and the results were presented in Table 4.

TABLE 4

| Varieties/ genotype | Total area harvested | Total herb distilled (kg) | Total Oil recovered (kg) | Estimated Oil yield/ha at pilot scale (kg) |
|---|---|---|---|---|
| Shivalik | 240 m2 | 456.0 | 3.3 | 137.5 |
| HY-77 | 240 m2 | 498.0 | 3.9 | 162.0 |
| Himalaya | 240 m2 | 624.0 | 4.7 | 195.0 |
| Gomti | 240 m2 | 606.0 | 3.0 | 125.0 |
| Kosi | 240 m2 | 618.0 | 6.0 | 250.0 |

EXAMPLE 5

Experiments on disease resistance were conducted and the reactions of some menthol min varieties/genotypes to leaf spot, rust and powdery mildew diseases, under field conditions were scored during 1997 (planting date 20$^{th}$ January) in CIMAP field station Pantnagar in Uttar Pradesh, India. Leaf spot and rust scored on modified 9 point disease scale. Where 1=0%, 2=1 to 5%, 3=6 to 10%, 4=11 to 20%, 5=21 to 30%, 6=31 to 40%, 7=41 to 60%, 8=61 to 80%, 9=81 to 100% foliage destroyed. Any variety/genotype was considered resistant when it showed resistance on 1 to 3 in scale. Powdery mildew scored on 1 to 5 scale and variety scoring 0 to 1 was considered resistant. Table 5 shows the results indicating relative resistance of the new genotype 'Kosi'.

TABLE 5

| Name of the variety/ | Disease score (Days after sowing) | | | | | | | | |
|---|---|---|---|---|---|---|---|---|---|
| geno- | Leaf spot | | | Rust | | | Powdery Mildew | | |
| type | 60 | 90 | 110 | 60 | 90 | 110 | 60 | 90 | 110 |
| Shivalik | 1.7 | 4.1 | 5.8 | 2.0 | 1.0 | 1.0 | 0.0 | 0.0 | 0.7 |
| HY-77 | 1.0 | 1.6 | 2.2 | 1.0 | 1.0 | 1.0 | 0.3 | 0.7 | 1.3 |
| Hima-laya | 1.0 | 1.3 | 1.8 | 1.0 | 1.0 | 1.0 | 0.0 | 0.3 | 0.7 |
| Gomti | 1.8 | 4.0 | 5.2 | 2.2 | 4.3 | 6.4 | 0.0 | 0.0 | 0.3 |
| Kosi | 1.0 | 1.4 | 1.6 | 1.0 | 1.0 | 1.0 | 0.0 | 0.0 | 0.3 |
| CD (5%) | 0.18 | 0.62 | 0.76 | 0.25 | 0.32 | 0.33 | 0.15 | 0.23 | 0.40 |

EVIDENCE OF UNIFORMITY AND STABILITY

Yield trials were conducted at different locations in India and the herbage, oil yield and methol content were observed to be higher (as in Tables 2, 3, & 4) in the new genotype 'Kosi', in comparison to other existing varieties. Similarly, no variants of any kind has been observed since 1994–95 indicating the stability and uniformity of the genotype. Further, the comparative herbage and oil yields of 'Kosi' were significantly higher in comparison to other varieties/genotypes in different years and seasons. Kosi requires somewhat high temperature for its sprouting from suckers and is suitable for late planting. Due to early maturing habit, there is not reduction in yield in the genotype (Example 4). The plant can be grown in monoculture and other crop may follow after harrowing the field with the disk harrow. Harrowing the field destroys the underground suckers leading to the cultivation of other crop.

Figure 2:
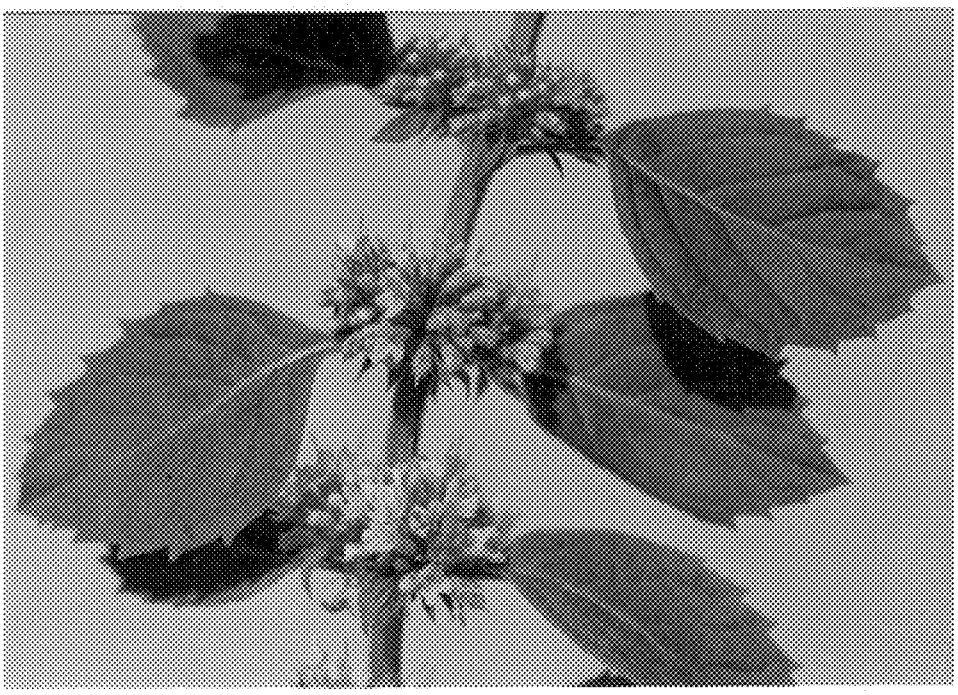
FIG. 2: shows the whitish purple florets of Kosi.
Figure 3:
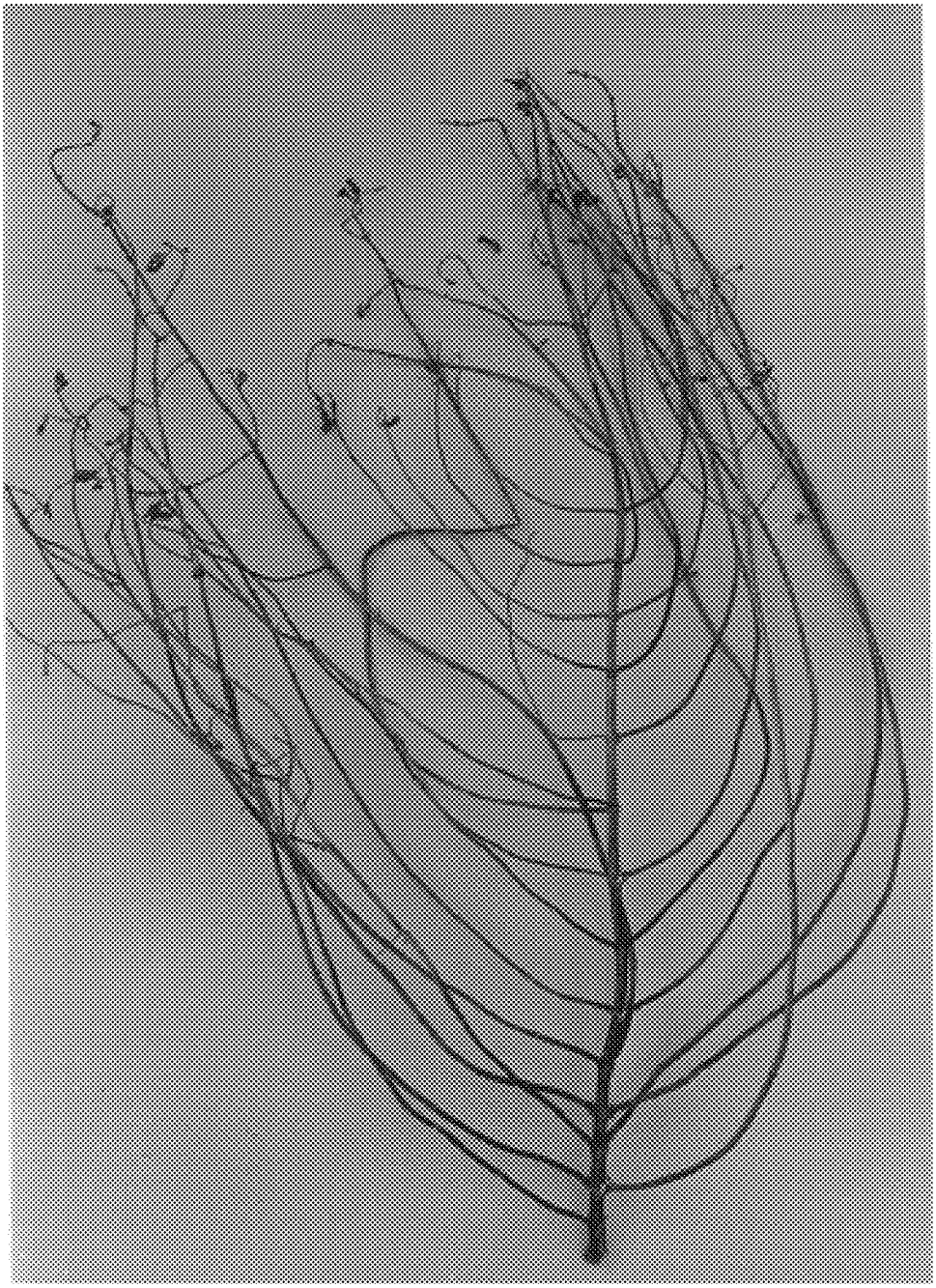
FIG. 3: shows a canopy of Kosi showing symmetrical branching.

The genotype 'Kosi' possessing light green leaves FIG. 1, whitish flowers, FIG. 2 has a distinct synchronous canopy, FIG. 3 characteristic to this genotype only. The genotype is having highest biomass and highest oil yield per hectare in comparison to others. The menthol content of the new genotype is higher (81 to 83%) in comparison to other genotypes.

RAPD ANALYSIS

The genotype 'Kosi' is distinct in its RAPD profile in comparison to CIMAP/HY-77, CIMAP/MASI, CIMAP/Shivalik, CIMAP/Gomti and CIMAP/Himalaya. Though the genotype was a half-sib of CIMAP/HY-77, still the RAPD pattern was different which indicates gross genome rearrangements in the new genotype, which could be considered as a transgressed macro-mutant.

The genotype CIMAP/Kosi or the variety 'Kosi' was developed at Central Institute of Medicinal and Aromatic Plants (CIMAP), Lucknow a constituent of the Council of Scientific and Industrial Research (CSIR), India under the genetic improvement program of mints. The complete RAPD profile for PCR amplified DNA using 12 primers is available providing evidence of distinctiveness of the genotype 'Kosi'.

We claim:

1. A new and distinct variety of mint plant, as herein described and illustrated.

* * * * *